United States Patent
Jenkins et al.

[11] Patent Number: 5,951,486
[45] Date of Patent: Sep. 14, 1999

[54] APPARATUS AND METHOD FOR ANALYSIS OF EAR PATHOLOGIES USING COMBINATIONS OF ACOUSTIC REFLECTANCE, TEMPERATURE AND CHEMICAL RESPONSE

[75] Inventors: Geoffrey Jenkins, Wellesley; Sandra Kimball, Boston; David Kunen, Wayland, all of Mass.

[73] Assignee: MDI Instruments, Inc., Woburn, Mass.

[21] Appl. No.: 09/177,924

[22] Filed: Oct. 23, 1998

[51] Int. Cl.$^6$ .................................................. A61B 5/00
[52] U.S. Cl. ............................................................ 600/559
[58] Field of Search ................................ 600/549, 559, 600/474

[56] References Cited

U.S. PATENT DOCUMENTS

| | | | |
|---|---|---|---|
| 4,334,538 | 6/1982 | Juhn | 604/35 |
| 5,626,139 | 5/1997 | Szeles et al. | 600/549 |
| 5,626,147 | 5/1997 | Lackey | 600/549 |
| 5,628,323 | 5/1997 | Pompei | 600/549 |
| 5,776,179 | 7/1998 | Ren et al. | 607/137 |

*Primary Examiner*—Cary O'Connor
*Assistant Examiner*—Pamela Wingood
*Attorney, Agent, or Firm*—Wolf, Greenfield & Sacks, P.C.

[57] ABSTRACT

A device provides an indication of a condition of an ear by combining measurements of temperature in the ear, acoustic reflectance of the ear, and/or a characteristic of any fluid in the ear. Any two of these measurements may be combined in the same device to provide improved diagnostic information. For example, chemical sensing of fluid may be combined with acoustic reflectometry or temperature sensing, or both, to provide improved diagnosis of ear pathologies. Acoustic reflectometry also may be combined with temperature sensing. Chemical sensing determines a characteristic of the fluid, such as whether a bacterium or a virus is present. The device may provide diagnostic information from sensed characteristics of the fluid, measured acoustic reflectance and/or measured temperature to indicate the risk of an ear infection. For example, the device may determine if any fluid present is infected. The device also may identify bacteria in the fluid. The temperature sensor also may be used to improve alignment between the device and the tympanic membrane, thus improving the accuracy of measurements.

22 Claims, 10 Drawing Sheets

| 430 ANGLE | BACTERIA/VIRUSES PRESENT | BACTERIA/VIRUSES ABSENT 434 |
|---|---|---|
| >95° | AOM LOW | OME LOW |
| 70° - 95° | AOM MODERATE | OME MODERATE |
| < 70° | AOM HIGH | OME HIGH |

Fig. 13

| 440 TEMPERATURE | BACTERIA/VIRUSES PRESENT | BACTERIA/VIRUSES ABSENT 444 |
|---|---|---|
| >100° | AOM HIGH | OME MODERATE |
| 99° - 100° | AOM MODERATE | OME MODERATE |
| < 99° | AOM MODERATE | OME LOW |

Fig. 14

| ANGLE/<br>TEMPERATURE | <99° | 99° - 100° | >100° |
|---|---|---|---|
| >95° | AOM LOW | AOM MODERATE | AOM MODERATE |
| 70° - 95° | AOM HIGH | AOM HIGH | AOM HIGH |
| < 70° | AOM HIGH | AOM HIGH | AOM HIGH |

Fig. 15A

| ANGLE/<br>TEMPERATURE | <99° | 99° - 100° | >100° |
|---|---|---|---|
| >95° | AOM LOW | AOM LOW | AOM LOW |
| 70° - 95° | AOM MODERATE | AOM MODERATE | AOM MODERATE |
| < 70° | OME HIGH | OME HIGH | AOM HIGH |

Fig. 15B

APPARATUS AND METHOD FOR ANALYSIS OF EAR PATHOLOGIES USING COMBINATIONS OF ACOUSTIC REFLECTANCE, TEMPERATURE AND CHEMICAL RESPONSE

BACKGROUND

One device that has become generally accepted and is commonly used by physicians and other health care professionals is known as a radiation thermometer, or infrared thermometer. Such devices are commercially available from Thermoscan, Inc. of San Diego, Calif. Devices of this type are described, for example, in U.S. Pat. Nos. 5,368,038 (Fraden), 4,797,840 (Fraden), 4,479,931 (Mooradian), 5,127,742 (Fraden), 5,178,464 (Fraden), 5,626,147 (Lackey), 4,895,164 (Wood), and 5,199,436 (Pompei). A radiation thermometer noninvasively detects thermal radiation from the tympanic membrane in order to determine the body temperature of the patient. A temperature reading made with this device may vary depending on the angle and depth of placement of the tip of the device with respect to the ear canal. In particular, the geometric relationship between the sensor and the tympanic membrane influences the ultimate reading by the sensor in operation. The field of view of the device when detecting thermal radiation also affects the temperature reading. The technology described in U.S. Pat. No. 5,626,147 (Lackey) seeks to solve these problems by using a sensor geometry which has wide and narrow fields of view and a look-up table with corrective values to provide an output indicative of the body temperature.

Another device that is used for diagnosis of ear pathologies is known as an acoustic reflectometer. Such devices are commercially available from MDI Instruments, Inc. of Woburn, Mass. under the trademarks "EARCHECK" and "EARCHECK PRO." Devices of this type are described, for example, in U.S. Pat. Nos. 4,601,295 (Teele), 4,459,966 (Teele), and 5,699,809 (Combs et al.), all of which are assigned to MDI Instruments, Inc. U.S. Pat. Nos. 5,594,174 (Keefe) and 5,651,371 (Keefe) also describe a device for measuring acoustic reflectance in a manner that permits the incident and reflected acoustic signals to be separately measured. An acoustic reflectometer measures sound waves emitted from the ear in response to a stimulus applied to the ear. The measured reflectance may be analyzed to determine the likelihood that fluid is present in the middle ear. Without correction or appropriate signal analysis, measurements made using an acoustic reflectometer also may be affected by line of sight from the tip of the device to the tympanic membrane. Although U.S. Pat. No. 5,699,809 (Combs et al.) describes a device in which the output is substantially independent of the line of sight, the device primarily determines the likelihood that fluid is present in the ear. However, in the detection of acute otitis media (AOM), otitis media with effusion (OME) or severe ear infection, the presence of fluid is only one factor in a diagnosis.

SUMMARY

A device provides an indication of a condition of an ear by combining measurements of temperature in the ear, acoustic reflectance of the ear, and/or a characteristic of any fluid in the ear. Any two of these measurements may be combined in the same device to provide improved diagnostic information. For example, chemical sensing of fluid may be combined with acoustic reflectometry or temperature sensing, or both, to provide improved diagnosis of ear pathologies. Acoustic reflectometry also may be combined with temperature sensing. Chemical sensing determines a characteristic of the fluid, such as whether a bacterium or a virus is present. The device may provide diagnostic information from sensed characteristics of the fluid, measured acoustic reflectance and/or measured temperature to indicate the risk of an ear infection. For example, the device may determine if any fluid present is infected. The device also may identify bacteria in the fluid. The temperature sensor also may be used to improve alignment between the device and the tympanic membrane, thus improving the accuracy of measurements.

Accordingly, in one aspect a medical instrument for analyzing an ear of a subject includes an array of chemical sensors and an acoustic reflectometer. The array of chemical sensors detects a characteristic of the fluid. The characteristic may be whether a bacterium or a virus is present. The acoustic reflectometer includes an acoustic transducer for generating acoustic waves at a plurality of frequencies and a microphone for receiving an acoustic signal corresponding to acoustic signals reflected from the ear to provide an output signal. The device coordinates measurements by the array of chemical sensors and acoustic reflectometer to provide an output indicative of a condition of the ear.

In another aspect, a medical instrument for analyzing an ear of a subject includes an array of chemical sensors and a temperature sensor. The array of chemical sensors detects a characteristic of the fluid. The characteristic may be whether a bacterium or a virus is present. The temperature sensor senses temperature in the ear and provides a signal indicative thereof. The device coordinates measurements by the array of chemical sensors and temperature sensor to provide an output indicative of a condition of the ear.

In another aspect, a medical instrument for analyzing an ear of a subject includes an array of chemical sensors, an acoustic reflectometer, and a temperature sensor. The array of chemical sensors detects a characteristic of the fluid. The characteristic may be whether a bacterium or a virus is present. The acoustic reflectometer includes an acoustic transducer for generating acoustic waves at a plurality of frequencies and a microphone for receiving an acoustic signal corresponding to acoustic signals reflected from the ear to provide an output signal. The temperature sensor senses temperature in the ear and provides a signal indicative thereof. The device coordinates measurements by the array of chemical sensors, acoustic reflectometer, and temperature sensor to provide an output indicative of a condition of the ear.

Similarly, another aspect is a process for analyzing an ear that includes chemical sensing of a characteristic of a fluid and measuring acoustic reflectance from an ear. Another aspect is a process for analyzing an ear that includes chemical sensing of a characteristic of fluid and detecting temperature in an ear. Another aspect is a process for analyzing an car that includes chemical sensing of a characteristic of a fluid, detecting temperature, and measuring acoustic reflectance from an ear. In one embodiment, the temperature sensor is a radiation thermometer. In another embodiment, temperature is sensed using a thermistor. Other kinds of temperature sensitive devices may be used.

The various combinations of measurements provide an indication of a risk of an ear infection. In particular, when bacteria and viruses and fluid are detected in the ear, an indication of a risk of an ear infection may be provided. When bacteria and viruses and elevated temperature are detected in the ear, an indication of a risk of an ear infection may be provided. When bacteria and viruses, elevated temperature, and fluid are detected in the ear, an indication of a risk of an ear infection may be provided.

BRIEF DESCRIPTION OF THE DRAWINGS

In the drawings:

FIG. 13 is an example look-up table for displaying the likelihood of an ear infection based on identification of a characteristic of a fluid and a measure of acoustic reflectance;

FIG. 14 is an example look-up table for displaying the likelihood of an car infection based on identification of a characteristic of a fluid and temperature; and FIGS. 15A and B provide an example look-up table for displaying the likelihood of an ear infection based on identification of a characteristic of a fluid, temperature and a measure of acoustic reflectance.

DETAILED DESCRIPTION

The following detailed description should be read in conjunction with the attached drawings in which similar reference numbers indicate similar structures. All references cited herein are hereby incorporated by reference.

A device provides an indication of a condition of ear by using two or more of the following: measuring temperature in the ear, measuring acoustic reflectance of the ear, and determining a characteristic of any fluid in the ear. The characteristic of the fluid may indicate whether the fluid is infected. The bacterial and viral composition of the fluid may be determined. By measuring temperature using an infrared sensor, or thermistor or other temperature sensitive device, body temperature may be determined. From acoustic reflectance measurements, the likelihood that fluid is present in the middle of the ear may be determined. A temperature measurement may be used to align the device with the tympanic membrane, thus improving the acoustic reflectance measurement. The combined measurements and the detected characteristic of the fluid, such as its bacterial and viral composition, also may be used together to enhance diagnosis of ear conditions. In particular, an elevated temperature with the presence of fluid that contains bacteria and viruses indicates a high risk of ear infection.

Figure 1:
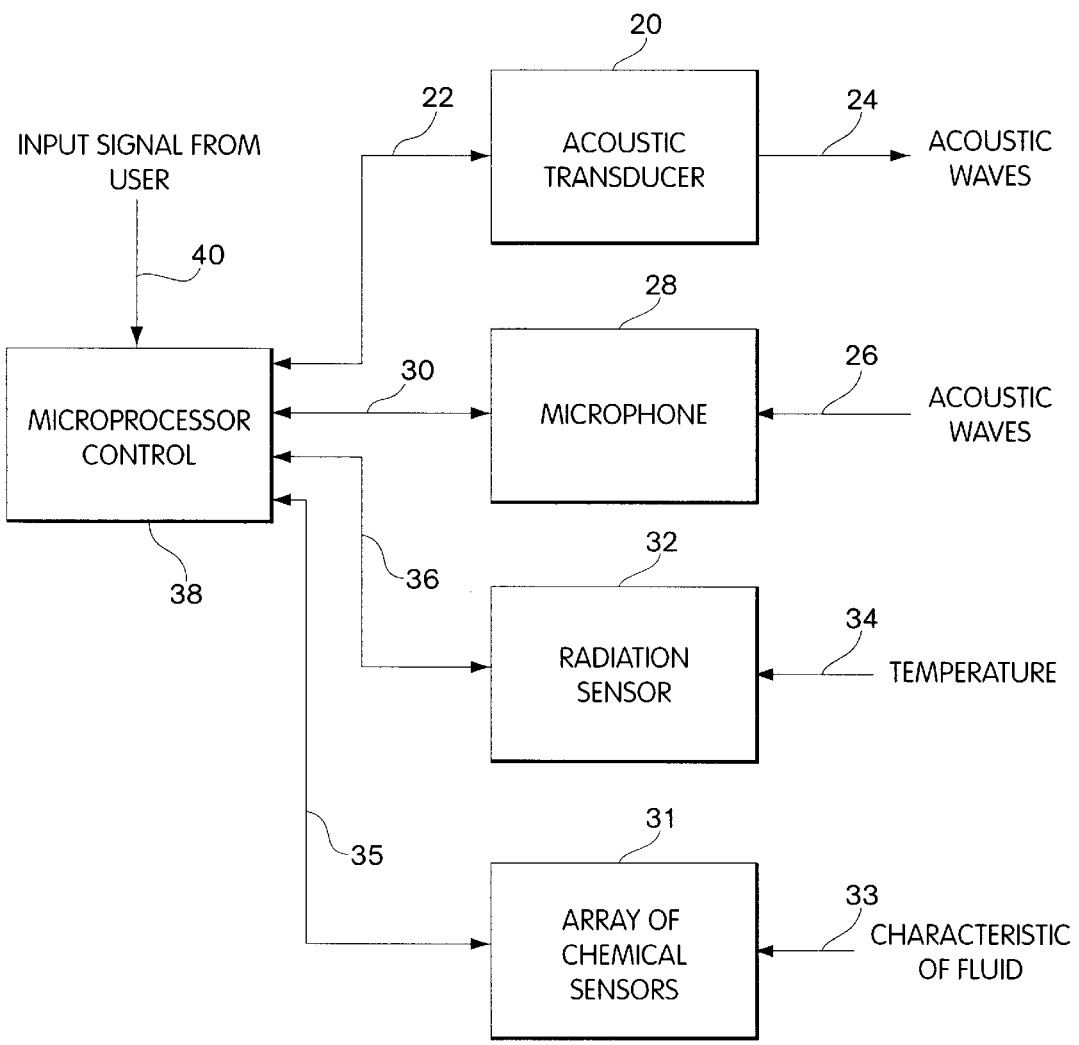
FIG. 1 is a block diagram of the electronic components of the combined array of chemical sensors, acoustic reflectometer and temperature sensor.

FIG. 1 illustrates a circuit diagram for a system in one embodiment. The system includes an acoustic transducer 20 which, in response to inputs 22 from a microprocessor controller 38, emits acoustic waves 24 into, for example, the ear canal. These incident acoustic waves 24 and reflected acoustic waves 26 are received by a microphone 28. In some embodiments, it is possible to separate the reflected acoustic waves from the incident acoustic waves. The microphone 28 provides this measurement to the microprocessor controller 38 as indicated at 30. A temperature sensor 32 senses temperature 34 in the ear and provides a signal 36 to the microprocessor controller 38. An array of chemical sensors 31 detects a characteristic of the fluid 33 in the ear and provides signal 35 to the microprocessor controller. For example, the array of chemical sensors may detect the presence of specific bacteria and viruses. The microprocessor controller 38 receives an input signal 40 from the user which indicates whether a reading should be taken. The microprocessor controller 38 then controls the acoustic transducer, microphone, temperature sensor, and array of chemical sensors to obtain data. The microprocessor controller 38 processes the data to provide results for display to the user, for example, according to the process described in FIG. 9 below.

A circuit such as shown in FIG. 1 is described in U.S. Pat. Nos. 4,459,966, 4,601,295, 5,594,174, 5,651,371, and PCT Application No. WO96/23293, cited above and U.S. patent application Ser. No. 09/006,543, filed Jan. 12, 1998, and U.S. patent application Ser. No. 09/012,695, filed Jan. 23, 1998, and PCT Application No. WO98/23205, published Jun. 4, 1998, and U.S. Pat. No. 5,699,809, issued Dec. 23, 1997, and hereby incorporated by reference. Other implementations also may be used.

Figure 2:
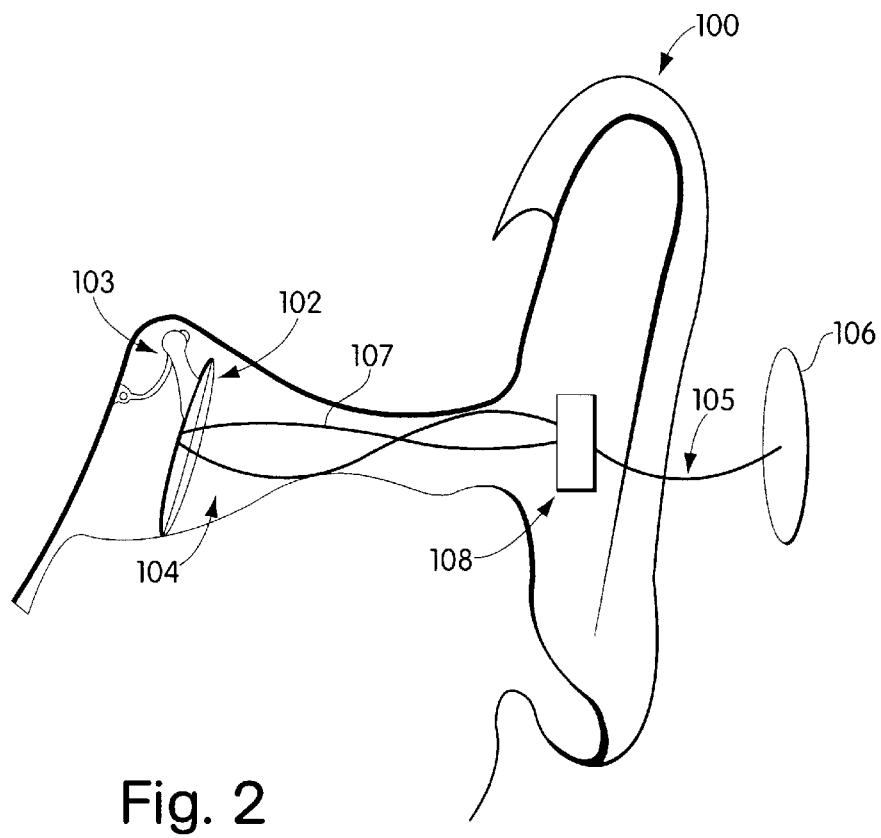
FIG. 2 is diagram illustrating acoustic reflectance of a healthy ear.

The process of measuring acoustic reflectance of an ear, in one embodiment, will first be described in connection with FIGS. 2–5. FIG. 2 shows a typical ear 100 having a tympanic membrane (an ear drum) 102, an ear canal 104, and middle ear 103. To measure acoustic reflectance, a low amplitude tone at a given frequency, indicated by line 105, is generated by an acoustic transducer, shown schematically at 106. The acoustic transducer generates sound waves for several frequencies, typically in the range of 500 Hertz to 20 kiloHertz, or more particularly, 1.8 kiloHertz to 4.4 kiloHertz. The low amplitude sound wave enters the ear canal and is incident on the ear drum 102. This sound wave is absorbed in part and reflected in part by the ear structures, including the tympanic membrane, oscicles, middle ear cleft and other components of the middle ear. The amplitude and phase of the reflected sound waves from these components are a function of the test frequency used and the complex acoustic impedance of the ear structures. In a healthy ear, some minimal reflection from the tympanic membrane and middle car is expected. The complex acoustic impedance of the middle ear, in turn, depends strongly on the conditions within the middle ear, and in particular on whether there is an effusion, such as fluid or abnormal pressure, in the middle ear. The vibration of a normal ear drum absorbs approximately half of the incident waves, resulting in weak reflected waves indicated by a line 107. A microphone 108 receives both the incident wave 105, the reflected wave 107 and reflected waves from ear components and as a result obtains a vector sum of the values. In other embodiments, the reflected sound may be separated from the incident sound.

Figure 3:
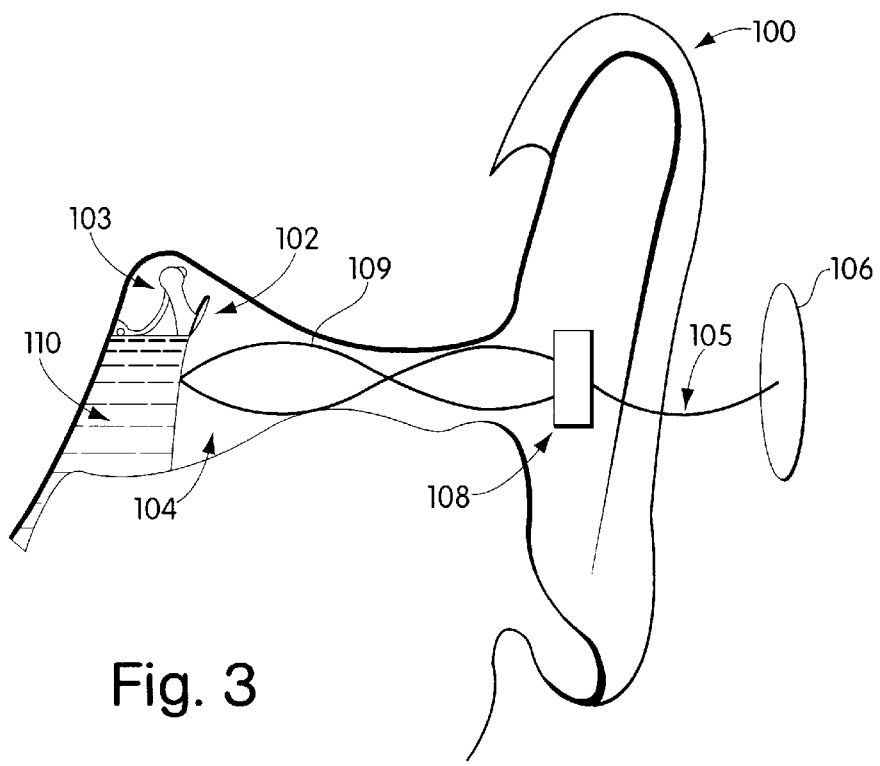
FIG. 3 illustrates acoustic reflectance and an ear having fluid behind the tympanic membrane.

Referring now to FIG. 3, an ear 100 is shown to have effusion 110. The middle ear effusion limits ear drum vibration, causing large reflected waves to have a larger amplitude as indicated at 109. The envelope of a vector sum of incident waves 105 and reflected waves 109, herein called an acoustic reflectance curve, has a null at the quarter wavelength points.

The shape of a region of the acoustic reflectance curve, defined by at least two points on the curve, is measured electronically to obtain an indicator of car condition which is substantially independent of the line of sight between the sound source and the tympanic membrane. The indicator may be a measure of the rate of change of the acoustic reflectance with respect to a change in frequency on either or both sides of the null, around the null, of other regions of the curve or of the entire curve. The area around the null is where the curve has a significant negative slope, defining entry into the null, to a point just before the null, and after the null, where the curve has a significant positive slope, defining the exit of the null. The null typically occurs near the resonance frequency of the ear. The significance of this measurement will now be described.

As the sound wave incident to the tympanic membrane approaches a frequency where its quarter waves are coincident, the amplitude of the vector sum of the reflected sound waves and the incident sound waves approaches a null. Generally speaking, normally conducting ear drums without fluid or abnormal pressure in the middle ear demonstrate a relatively shallow acoustic null. Conversely, fluid or abnormal pressure in ears causes a stronger reflection and therefore a deeper acoustic null. The depth of this null is dependent, however, on the line of sight to the eardrum. It has been discovered, however, that the rate of change of the acoustic reflectance between the entry into the null and the exit from the null is steeper for ears having middle ear fluid or pressure than for healthy ears. It was further discovered that differences in this rate of change due to changes in line of sight have less of an impact on the indication of the presence of an effusion or abnormal pressure.

Eardrums that are free to vibrate with the incident sound wave (i.e., healthy) produce not only a less deep null but also a less steep slope at frequencies around the null and thus a larger spectral gradient angle. The restrained motion produces lower reflectance values relative to the null at nearby frequencies and therefore an apparent lower slope.

When the eardrum motion is restrained (i.e., the ear is not healthy), the slope around the null is steeper. Because acoustic reflectance is related to the complex acoustic impedance of the tympanic membrane, the measure of its rate of change with respect to frequency input is analogous to measuring the "Q" of an electrical circuit. Thus, restraining the car drum results in both a higher acoustic impedance and a sharper "Q." The "Q" is relatively constant for a given impedance regardless of variations in the amount of energy incident because of line of sight limitations.

Figure 4:
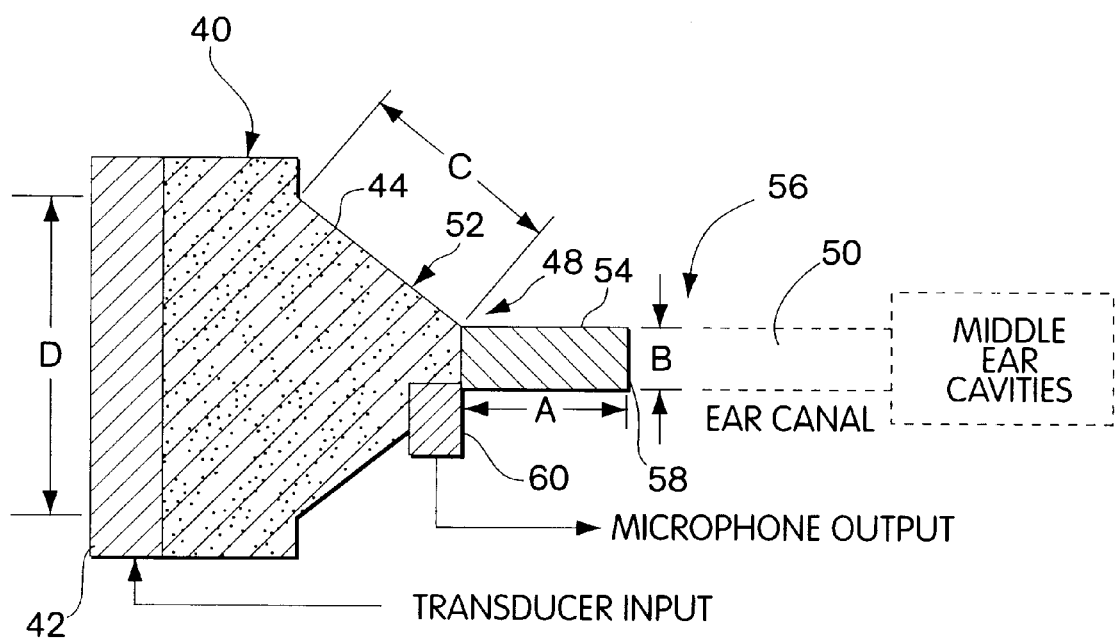
FIG. 4 is a diagram of test head that may be used for acoustic reflectance.

A device for one embodiment will now be described. FIG. 4 is a cross sectional diagram of a test head for an instrument in one embodiment. The test head 40 includes a transducer 42 that creates a sound field in sound cavity 44. Sound in the cavity 44 is channeled through probe 48 to the vicinity of the ear canal 50. The probe has a funnel-shaped section 52 and an optional linear section 54. The dimensions of section 54 may be chosen to match the dimensions of the typical ear canal under test. This section matches the impedance of the probe tip and the typical ear canal. For children's ears, length A of the linear portion 54 of the probe preferably is equal to approximately 1 cm and inner diameter B of the same section should be in the range of approximately 0.25 to 0.75 cm. Similarly, good results are obtained when length C along the side of funnel-shaped section 52 of the probe is about 5 cm and the approximate outer diameter D of the large end of the probe which is in contact with the sound cavity wall is approximately 7 cm. With appropriate compensation, tips with other exit diameters may be used. The probe extension does not need to be inserted into the ear canal. In practice, there may be a narrow gap 56 between the test head probe tip 58 and the entrance to the ear canal 50. Control of this gap may be facilitated by a response rubber spacer (not shown) attached at the end of probe tip 58.

The incident sound wave created by transducer 42 in the test head emanates from the test head at the tip 58 of the probe 48 and enters the ear canal 50. Thereafter, a portion of the incident wave is reflected by structures of the ear. Minimal reflection from a healthy ear can be suppressed by suitable selection of the inner probe tip diameter, e.g., by enlarging it to 1.0 cm for children.

Portions of the reflected waves enter at tip 58 into the hollow linear portion 54 of the test head. The microphone 60 is located within the test probe 48 at the junction of the linear portion of 54 and the funnel-shaped section 52. As a result, the microphone 60, in effect, measures the net sound pressure at this point; this net sound pressure is the vector sum of the incident and reflected signals. In order to reduce internal sound reflection and resonances within the test head, the sound cavity 44 may be filled with acoustic absorbing materials.

In other embodiments, a transfer function describing the acoustic characteristics of the ear may be determined and used as the basis for a diagnosis.

Figure 5:
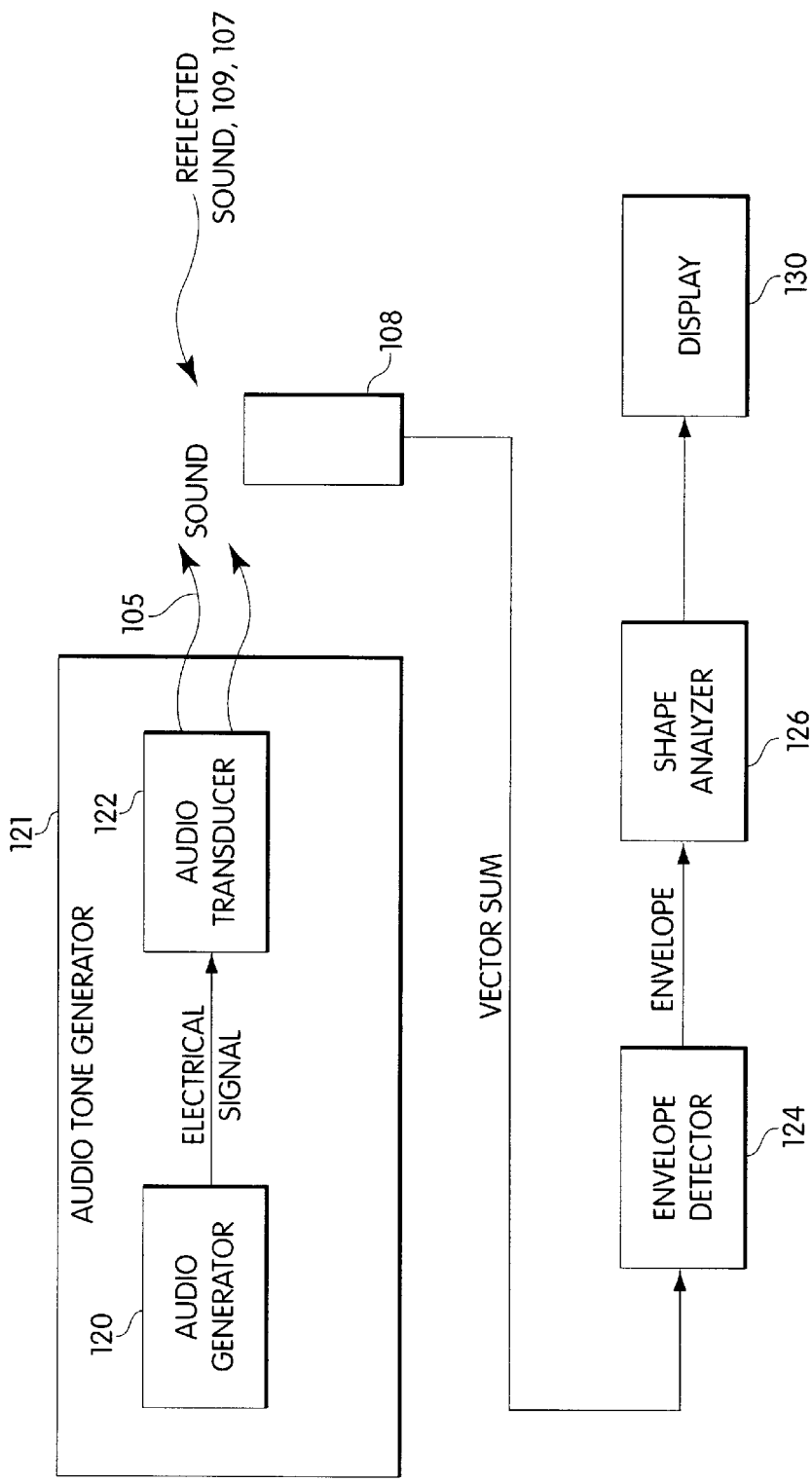
FIG. 5 is a block diagram describing an electronic circuit for measuring acoustic reflectance.

Having now described the general principles for measuring acoustic reflectance, and a suitable test head for use in an acoustic reflectometer, electronic circuitry suitable for an embodiment will now be described in connection with FIG. 5. FIG. 5 is a general block diagram of a device of one embodiment, including its electrical and mechanical components. The components of this circuit may be implemented using a microprocessor, except for the display, acoustic transducer and microphone. An analog implementation also may be made. In FIG. 5, an audio tone generator 121 includes an audio generator 120, which produces an electrical signal which is applied to an audio transducer 122 (such as transducer 42 in the test head of FIG. 4). The audio transducer, in response to the electrical signal, generates a low level acoustic sound wave (105 in FIGS. 2 and 3) which is applied to the outer ear canal. The audio transducer 122 may be an electronic earphone, electromagnetic earphone, or other type of transducer. The transducer may be a small loudspeaker such as used in high fidelity sound headsets.

A portion of the incident sound wave is reflected by ear structures as described above. In this embodiment, these reflected waves are summed with an incident wave by microphone 108 (such as microphone 60 of the test head of FIG. 4). The microphone may be a condenser microphone, an electrostatic microphone or other kind of microphone. In this embodiment, the signal output by the microphone represents the vector sum of the incident wave and the reflected sound waves, having a voltage which is inversely proportional to the amplitude of the reflected waves.

An envelope detector 124 converts the vector sum represented by the signal output by the microphone to an envelope signal represented by a voltage which varies with the frequency of the incident wave. The envelope detector 124 may be implemented as a peak value envelope detector, a root-mean square (RMS) voltage detector, or analog-to-digital converter, such as part of a suitably programmed microprocessor. In one embodiment described in more detail below, the envelope is detected using information about the frequency spectrum of the vector sum. The envelope so detected is called the acoustic reflectance curve.

A shape analyzer 126 measures the shape of a region of the acoustic reflectance curve to obtain an indicator of ear condition which is substantially independent of the line of sight from a sound source to the tympanic membrane. This information may be one or more measures of the shape of the envelope including a measure of the rate of change of acoustic reflectance with respect to a change in frequency around the null, on either side of the null or on a region of the curve or of the entire curve. This measure, for example, may be an angle, gradient, slope, width, or other measure of the shape of the acoustic reflectance curve determined in a manner to be described below. This information is then displayed in a suitable format by display section 130.

In FIG. 5, a memory (not shown) may be added to store results of processing of one acoustic reflectance curve. With such a memory, the circuit may be operated to perform automatically a number of tests sequentially on the ear. The best results for the sequence of tests may be kept and the others may be discarded. For example, the best results could be defined as the measurement of the shape of the acoustic reflectance curve having the deepest null value. In this manner, a user of the device may attempt to obtain the best result with minimal effort. The use of this memory is described below in more detail in connection with FIG. 9.

Having now described an embodiment of an acoustic reflectometer, the temperature sensor will now be described. In one embodiment, the temperature sensor is implemented as a radiation sensor as shown in U.S. Pat. Nos. 5,626,147; 5,368,038; 5,199,436; 5,178,464; 5,127,742; 4,797,840; and 4,479,931, cited above and hereby incorporated by reference. Other embodiments of radiation sensors are known and also may be used. Other kinds of temperature sensors include thermistors and other temperature sensitive devices.

One embodiment of the radiation thermometer uses a sensor system that compensates for different ear canal placement geometries by creating an IR signal collected via both wide and narrow fields of view. By using IR information that is responsive to a wide field of view in conjunction with information from a narrow field of view, the errors in temperature reading occasioned by the vagaries in probe positioning in the ear can be compensated by appropriately programmed signal adjustment. Specifically, the signal processor integrated with the sensor weights the input from both sources and using a look-up table, applies corrective values to give an accurate and repeatable temperature measurement. This value also is indicative of alignment of the device with the ear.

Figure 6:
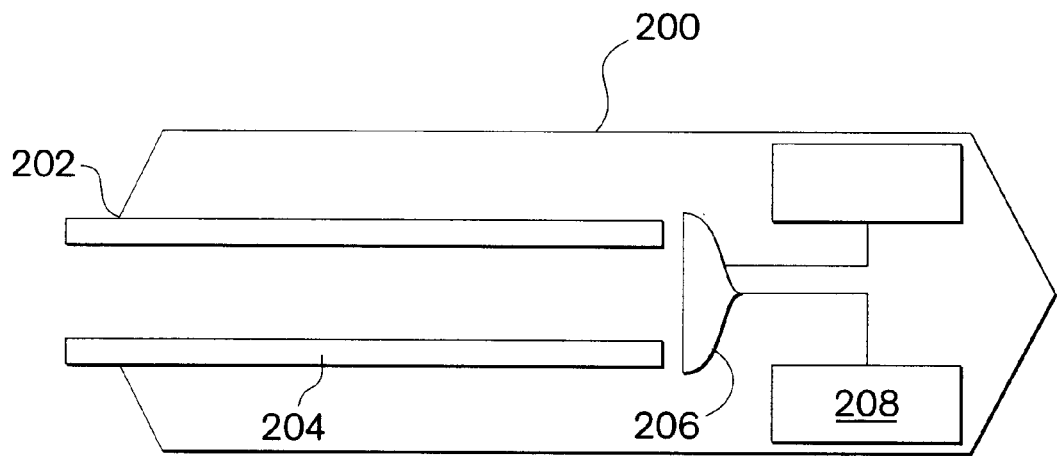
FIG. 6 is a diagram illustrating a radiation thermometer.

FIG. 6 provides a simplified diagram of elements in one embodiment of an IR thermometer. In this illustrative diagram, the thermometer device provides a housing 200 for the operative elements of the device. The housing has a terminus end at which an IR receiving opening 202 is positioned to feed incoming radiation to a wave guide 204. There are a variety of possible wave guides available for use that offer different performance characteristics such as distortion, ranging from smooth gold-plated tubes to fiber optic bundles. In functional terms, the wave guide is designed to collect and pass incoming radiation undisturbed to IR sensor 206. Again, there are several choices in sensor systems, including thermopile types and pyroelectric elements. In the embodiment to be described, the sensor is a pyroelectric sensor, which uses "matched pairs" to cancel out signal contributions intrinsic with the pyroelectric elements.

Continuing with FIG. 6, the sensor 206 is connected to processor 208 for converting the IR data into a high quality temperature reading as well be described in more detail below. The sensor design may be such that it provides signals for both wide and narrow fields of view. These signals are provided by creating two or more sensors, each reporting separately to the processor information on radiation.

Figure 7:
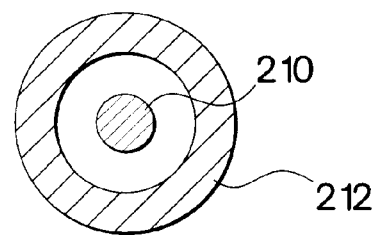
FIG. 7 is a diagram illustrating two sensors for use with radiation thermometry.

Such a sensor geometry is depicted in FIG. 7. More specifically, the sensor 206 of FIG. 5 is, in fact, two separate sensors, 210 and 212, each connected to the processor 208. The first sensor 210 is relatively smaller and concentric to the center line of the wave guide 204, thus providing a narrow field of view. The outer sensor 212, on the other hand, is somewhat larger and positioned outside the perimeter of the wave guide, thereby providing a relatively wider field of view.

This kind of radiation thermometer, or other type, may be used in combination with an acoustic reflectometer. The uncorrected temperature or output of two radiation sensors may be used to provide alignment for acoustic measurement.

With either an acoustic reflectometer or temperature sensor, or both, an array of chemical sensors may be used. An array of sensors can be used to analyze the chemical composition of fluids. The fluids may be gaseous in nature. Devices of this type are described in U.S. Pat. Nos. 5,571, 401 (Lewis) and 5,5,698,089 (Lewis), assigned to the California Institute of Technology. The sensors are resistors made of alternating conductive and non-conductive materials whose resistance varies in the presence of specific compounds. The resistors have a different resistance when contacted with a fluid comprising a chemical analyte at a first concentration, than when contacted with a fluid comprising the chemical analyte at a second, different concentration. Leads attached to the sensors are connected to an electrical measuring device. The device measures changes in resistivity at each sensor of the array over time. An array of chemical sensors may be implemented in many ways to provide an analysis a characteristic of fluid, such as bacterial or viral content, behind the middle of the ear to the microprocessor controller.

Figure 8:
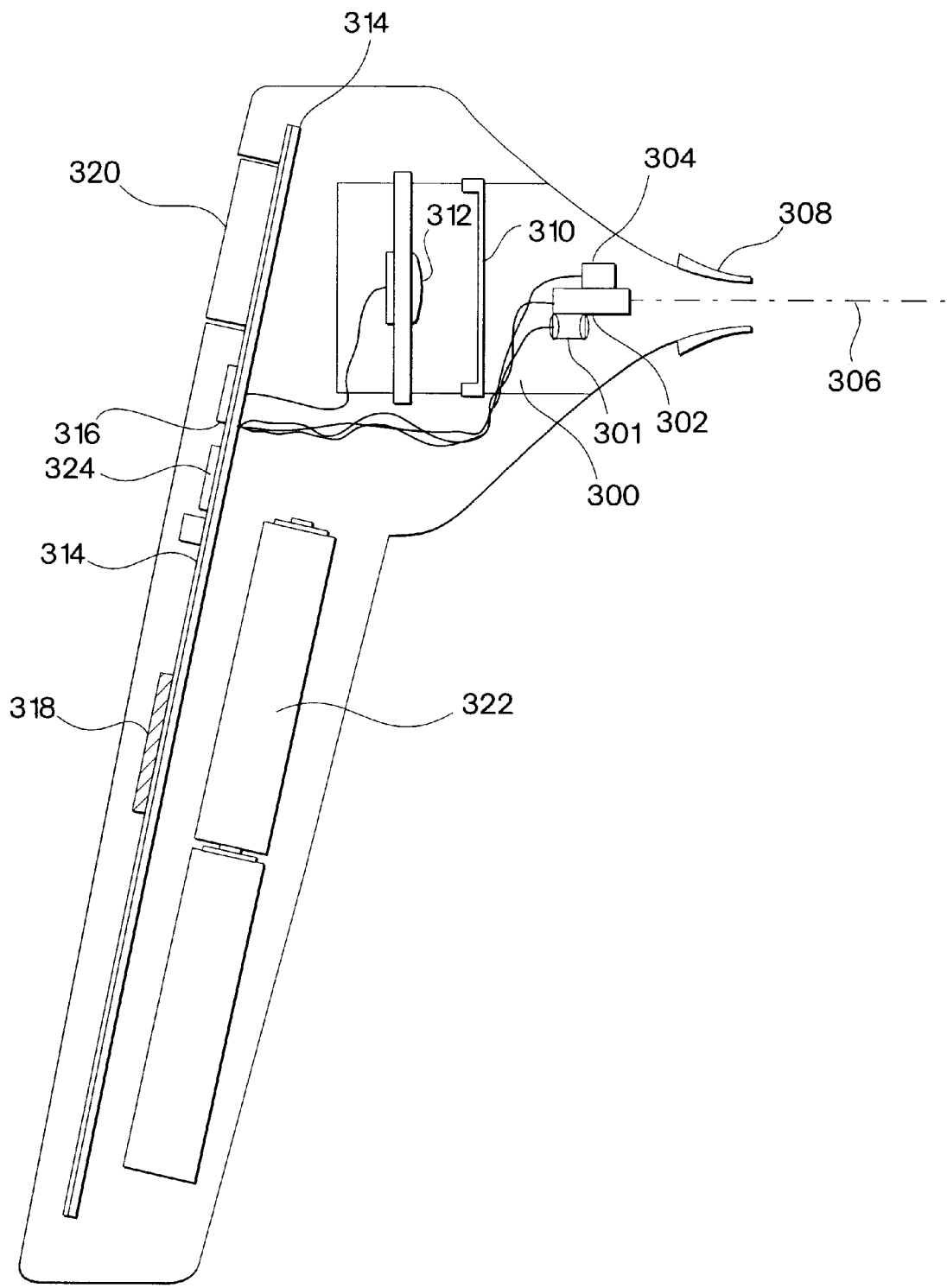
FIG. 8 is a diagram illustrating the physical layout of the array of chemical sensors, microphone of the acoustic reflectometer, and the temperature sensor within the acoustic chamber in one embodiment.

The physical arrangement of the microphone, temperature sensor, and array of chemical sensors within an acoustic chamber in a device will now be described in more detail in connection with FIG. 8. FIG. 8 shows a cross section of a device in one embodiment. The device includes an acoustic chamber 300 in which a temperature sensor 302, array of chemical sensors 301, and microphone 304 are disposed. The temperature sensor 302 is aligned with an axis 306 through the tip 308 of the device. An acoustic resistor 310 and speaker 312 generate the acoustic waves out of the device. The device also includes a printed circuit board 314 which includes analog circuitry 316 for processing and controlling the speaker, microphone, array of chemical sensors, and temperature sensor. The device may be powered by batteries 322. A microprocessor 318 is used to process these results and generate output to a user using the LCD display 320, in response to the user pressing an input button 324. Suitable designs for the LCD display include a display of temperature, a measure of the likelihood of fluid being present in the ear and/or a characteristic of the fluid, such as described in the patents cited above. The device may be calibrated in the manner described in U.S. Pat. No. 5,699,809.

Figure 9:
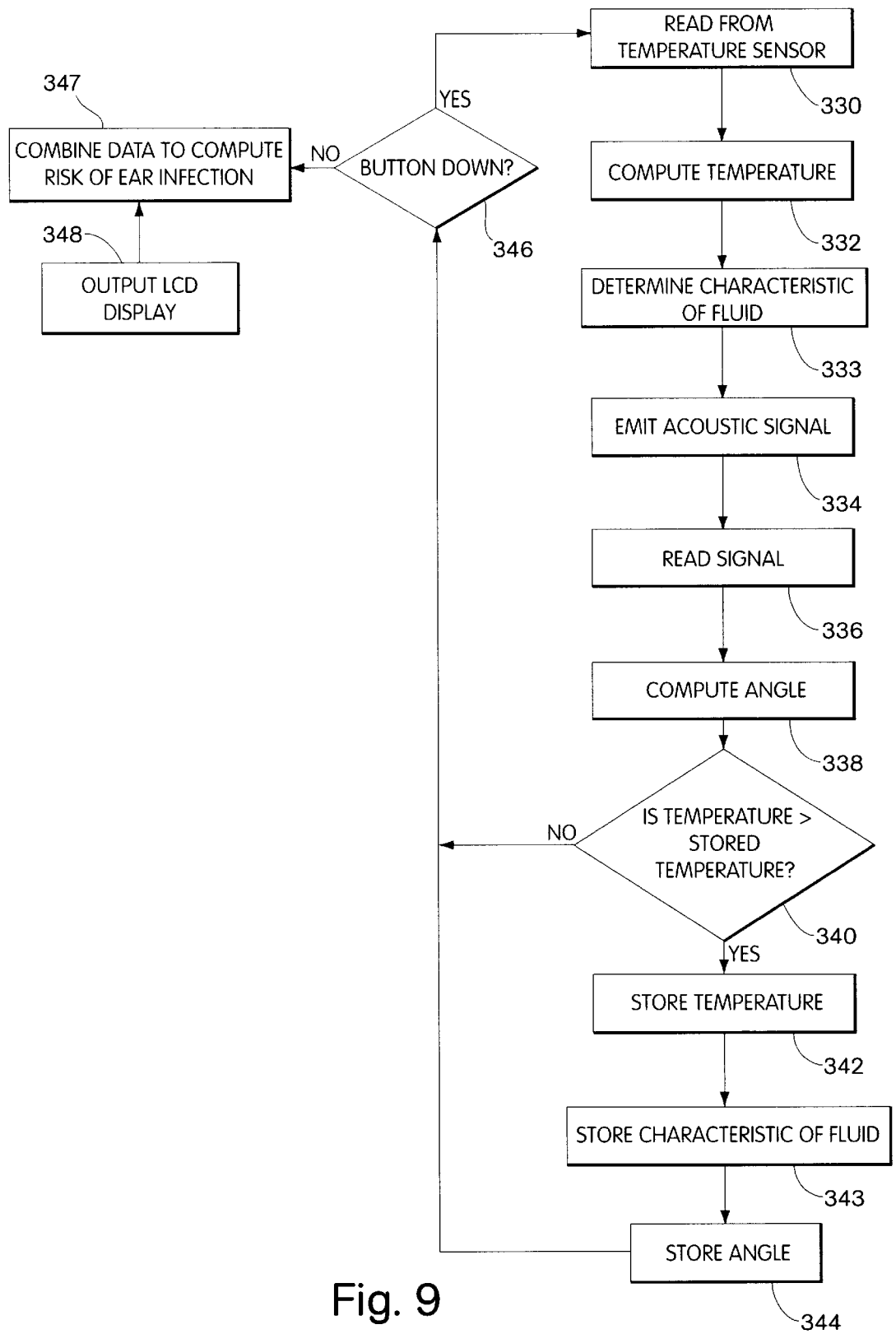
FIG. 9 is a flow chart describing how readings from the array of chemical sensors, temperature sensor, and microphone are coordinated to provide an output to a user.

FIG. 9 is a flow chart describing how the microprocessor controller 38 (FIG. 1) coordinates the reading of information from the microphone, array of chemical sensors, and temperature sensor to provide an output to the user. So long as the user is providing an input signal indicating a reading should be taken, for example by pressing the input button, data from the temperature sensor is read in step 330. The user should rotate the device with the tip against the opening to the ear canal while pressing the button. Any lobe of the ear also may be pulled lightly back to help align the device. An uncorrected temperature is then computed from the temperature sensor data using known techniques in step 332. A characteristic of the fluid, such as its bacterial and viral content, is then computed from the chemical sensor data using known techniques in step 333. The acoustic signal is also emitted in step 334 and a signal is read from the microphone in step 336. A measure of the likelihood of the presence of fluid is then determined in step 338. For example, this measure may be determined by computing the measure of the shape of the acoustic reflectance curve, or by measuring the peak of the acoustic reflectance curve. If the temperature computed in step 332 is greater than any stored temperature, as determined in step 340, the currently measured temperature is stored in step 342, determined characteristic of the fluid is stored in step 343, and the computed acoustic reflectance measure also is stored in step 344. Alternatively, in step 340, a minimized angle or peak value may be used. If the user input signal still indicates a reading should be taken, as determined in step 346, the process of steps 330–344 is repeated. Otherwise, a measure of the likelihood of the presence of a middle ear infection is then determined in step 347. The resulting output is provided to the LCD display in step 348, possibly providing a corrected temperature as shown in U.S. Pat. No. 5,626,147.

The combination of an array of chemical sensors, a temperature sensor, and acoustic reflectometer improves the accuracy of the device with respect to the line of sight to the tympanic membrane and provides enhanced diagnostic utility. The determination of the presence or absence of an abnormal temperature in conjunction with the determination of the likelihood of presence of fluid that is infected may assist a physician in the diagnosis of an acute otitis media with an effusion. In particular, an elevated temperature and the presence of fluid containing bacteria and viruses indicate a high risk of ear infection.

The measured temperature, the measure related to acoustic reflectance, such as an angle, and the measures related to characteristic of the fluid may be displayed separately and/or may be combined to provide an additional diagnostic measure. This diagnostic measure may be computed in many ways, such as a look up table that maps ranges of bacterial and viral content, temperature, and acoustic reflectance to the likelihood that an ear infection is present.

There are numerous display formats ranging from quantitative numerical readings to ranges of risk level. For example, the quantitative readings shown in FIGS. 10, 11, and 12, and the ranges of risk level shown in FIGS. 13, 14, and 15A–B may be displayed to a user, as described below. Alternatively, the absolute values of temperature and acoustic reflectance, and the bacterial and viral content also could be displayed to the user.

Figure 10:
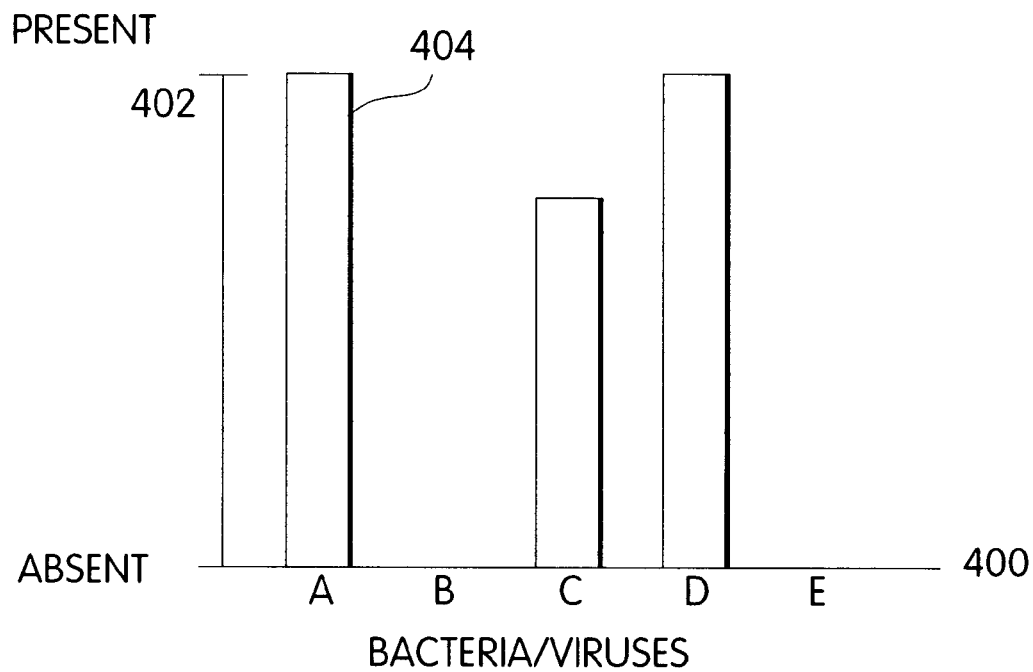
FIG. 10 is an example output of the readings determined by a device that performs chemical sensing of a characteristic of a fluid.

Referring now to FIG. 10, where the characteristic of the fluid is the presence of a bacterium and/or a virus, the presence of the bacterium or virus may be displayed by a bar chart. On the horizontal axis 400 an indicator for each bacterium or virus is shown. On the vertical axis of 402, a range of values indicating the presence or absence of the bacterium or virus is provided. Associated with each bacterium or virus is a value, e.g., 404, indicating the likelihood of presence of that bacterium in any fluid in the ear.

Figure 11:
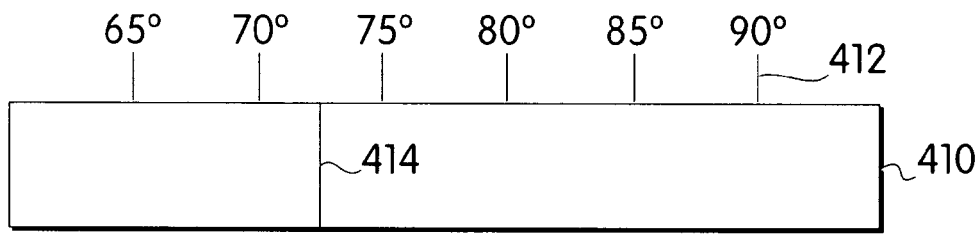
FIG. 11 is an example output of the readings determined by a device that measures acoustic reflectance.

Referring now to FIG. 11, the spectral gradient angle may be displayed using a bar 410 demarcations 412, each of which is associated with an angle. A line 414 is displayed on the bar 410 to indicate the computed angle.

Figure 12:
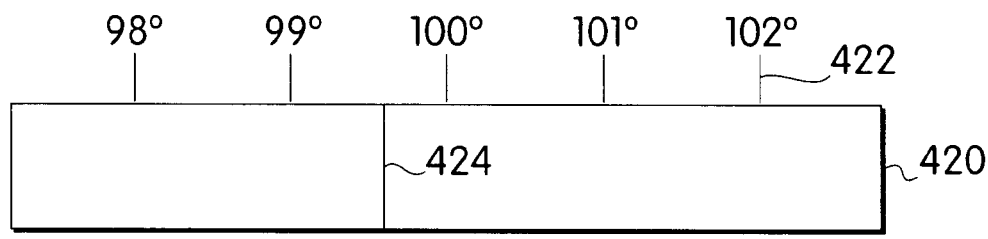
FIG. 12 is an example output of the readings determined by a device that measures temperature.

Referring now to FIG. 12, the temperature may be displayed using a similar scale or bar as shown at 420. Demarcations 422 are provided, each of which is associated with a temperature. A line 424 is displayed on the bar 420 to indicate the measured temperature.

FIG. 13 is a table 430 illustrating ranges of risk level, which may be displayed to a user, for a device that combines an array of chemical sensors with acoustic reflectometry. Each row 432 is associated with a range of spectral gradient angles. Each column 434 is associated with the presence or absence of a bacterium or virus.

Referring now to FIG. 14, a similar table 440 may be displayed to a user for a device that combines an array of chemical sensors with thermometry. In particular, each row 442 is associated with a range of temperatures. Each column 444 is associated with the presence or absence of a bacterium or virus, or if no fluid is present.

Referring now to FIGS. 15A and B, tables 450 and 452 may be displayed as the output of a device that combines an array of chemical sensors with both acoustic reflectometry and thermometry. FIG. 15A is a display shown if a bacterium or a virus is present. FIG. 15B is a display shown if a bacterium or a virus is not present. Each row 454 is associated with a range of spectral gradient angles. Each column 456 is associated with ranges of temperatures.

The value in each cell in the tables in FIGS. 13, 14 and 15A–B indicates the level of risk (either low, moderate or high) of otitis media with effusion (OME) or acute otitis media (AOM). Many other displays may be provided. For example, the determined level of risk may be displayed to the user instead of the table used to obtain the level of risk. Such a display provides an improved diagnostic measure for evaluating the risk of these and other ear pathologies.

Having now described a few embodiments, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention.

What is claimed is:

1. A medical instrument for analyzing an ear of a subject, comprising:

an array of chemical sensors responsive to a characteristic of a fluid to provide a first output signal indicative thereof; and an acoustic reflectometer comprising an acoustic transducer for generating acoustic waves at a plurality of frequencies and a microphone for receiving acoustic signals reflected from the ear to provide a second output signal; and a controller connected to the array of chemical sensors and the acoustic reflectometer to control acquisition of the first and second output signals.

2. The medical instrument of claim 1, wherein the characteristic of the fluid is the presence of a bacterium in the fluid.

3. The medical instrument of claim 2, further comprising:
means for indicating to the user when both fluid and a bacterium are detected in the car.

4. The medical instrument of claim 1, wherein the characteristic of the fluid is the presence of a virus in the fluid.

5. The medical instrument of claim 4, further comprising:
means for indicating to the user when both fluid and a virus are detected in the car.

6. The medical instrument of claim 1, further comprising:
means for indicating to the user when both fluid and a negative characteristic of the fluid are detected in the ear.

7. A medical instrument for analyzing an car of a subject, comprising:
an array of chemical sensors responsive to a characteristic of a fluid to provide a first output signal indicative thereof;
a temperature sensor for sensing temperature in the ear and providing a second output signal indicative thereof; and
a controller connected to the array of chemical sensors and the temperature sensor to control acquisition of the first and second output signals.

8. The medical instrument of claim 7, wherein the characteristic of the fluid is the presence of a bacterium in the fluid.

9. The medical instrument of claim 8, further comprising:
means for indicating to the user when an elevated temperature and a bacterium are detected in the ear.

10. The medical instrument of claim 7, wherein the characteristic of the fluid is the presence of a virus in the fluid.

11. The medical instrument of claim 10, further comprising:
means for indicating to the user when an elevated temperature and a virus are detected in the ear.

12. The medical instrument of claim 7, further comprising:
means for indicating to the user when an elevated temperature and a negative characteristic of the fluid are detected in the ear.

13. A medical instrument for analyzing an ear of a subject, comprising:
an array of chemical sensors responsive to a characteristic of a fluid to provide a first output signal indicative thereof; and
an acoustic reflectometer comprising an acoustic transducer for generating acoustic waves at a plurality of frequencies and a microphone for receiving acoustic signals reflected from the ear to provide a second output signal;
a temperature sensor for sensing temperature in the ear and providing a third output signal indicative thereof; and
a controller connected to the array of chemical sensors and the temperature sensor.

14. The medical instrument of claim 13, wherein the characteristic of the fluid is the presence of a bacterium in the fluid.

15. The medical instrument of claim 14, further comprising:
means for indicating to the user when an elevated temperature and a bacterium are detected in the ear.

16. The medical instrument of claim 14, further comprising:
means for indicating to the user when both fluid and a bacterium are detected in the ear.

17. The medical instrument of claim 13, wherein the characteristic of the fluid is the presence of a virus in the fluid.

18. The medical instrument of claim 17, further comprising:
means for indicating to the user when an elevated temperature and a virus are detected in the ear.

19. The medical instrument of claim 17, further comprising:
means for indicating to the user when both fluid and a virus are detected in the ear.

20. The medical instrument of claim 13, further comprising:
means for indicating to the user when an elevated temperature and a negative characteristic of the fluid are detected in the ear.

21. The medical instrument of claim 13, further comprising:
means for indicating to the user when both fluid and a negative characteristic of the fluid are detected in the ear.

22. The medical instrument of claim 13, further comprising:
means for analyzing the first, second and third output signals to provide an indication of risk of ear infection according to detected temperature, any detected fluid and any detected characteristic of the fluid.

* * * * *